US012758762B2

(12) United States Patent
Beekman et al.

(10) Patent No.: US 12,758,762 B2
(45) **Date of Patent: *Oct. 13, 2026**

(54) PERCUTANEOUS CIRCULATORY SUPPORT DEVICE INCLUDING PROXIMAL PRESSURE SENSOR

(71) Applicant: Boston Scientific Scimed Inc., Maple Grove, MN (US)

(72) Inventors: Darrin Dale Beekman, Osseo, MN (US); Maren Landree, Medina, MN (US); Travis J. Schauer, Rockford, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 277 days.

This patent is subject to a terminal disclaimer.

(21) Appl. No.: 18/222,206

(22) Filed: Jul. 14, 2023

(65) Prior Publication Data

US 2024/0017053 A1 Jan. 18, 2024

Related U.S. Application Data

(60) Provisional application No. 63/390,054, filed on Jul. 18, 2022.

(51) Int. Cl.

*A61M 60/531* (2021.01)
*A61M 60/237* (2021.01)
*A61M 60/13* (2021.01)

(52) U.S. Cl.

CPC ........ *A61M 60/531* (2021.01); *A61M 60/237* (2021.01); *A61M 60/13* (2021.01)

(58) Field of Classification Search

CPC .. A61M 60/13; A61M 60/221; A61M 60/237; A61M 60/419; A61M 60/531;
(Continued)

(56) References Cited

U.S. PATENT DOCUMENTS

| | | |
|---|---|---|
| 4,957,504 A | 9/1990 | Chardack |
| 5,527,159 A | 6/1996 | Bozeman, Jr. et al. |

(Continued)

FOREIGN PATENT DOCUMENTS

| | | |
|---|---|---|
| EP | 847767 B1 | 2/2005 |
| EP | 2301598 B1 | 7/2017 |

(Continued)

OTHER PUBLICATIONS

US 9,067,007 B2, 06/2015, Tanner et al. (withdrawn)

(Continued)

*Primary Examiner* — Michael T Rozanski
(74) *Attorney, Agent, or Firm* — Seager, Tufte & Wickhem LLP

(57) ABSTRACT

A percutaneous circulatory support device includes a housing and an impeller disposed within the housing. The impeller is configured to rotate relative to the housing to cause blood to flow through the housing. A motor is operably coupled to the impeller, and the motor is configured to rotate the impeller relative to the housing. A catheter is coupled to the motor. A collar is coupled to the catheter and disposed proximally relative to the housing. The collar includes an internal chamber, and pressure sensor is disposed within the internal chamber of the collar.

20 Claims, 7 Drawing Sheets

(58) Field of Classification Search
CPC ......... A61M 60/816; A61B 2562/0247; A61B 5/0215; A61B 5/6852
See application file for complete search history.

(56) References Cited

U.S. PATENT DOCUMENTS

| | | | |
|---|---|---|---|
| 5,692,882 | A | 12/1997 | Bozeman, Jr. et al. |
| 5,947,892 | A | 9/1999 | Benkowski et al. |
| 5,964,694 | A | 10/1999 | Siess et al. |
| 6,007,478 | A | 12/1999 | Siess et al. |
| 6,135,729 | A | 10/2000 | Aber |
| 6,139,487 | A | 10/2000 | Siess |
| 6,176,822 | B1 | 1/2001 | Nix et al. |
| 6,176,848 | B1 | 1/2001 | Rau et al. |
| 7,010,954 | B2 | 3/2006 | Siess et al. |
| 7,841,976 | B2 | 11/2010 | McBride et al. |
| 7,927,068 | B2 | 4/2011 | McBride et al. |
| 7,972,122 | B2 | 7/2011 | Larose et al. |
| 8,376,707 | B2 | 2/2013 | McBride et al. |
| 8,591,393 | B2 | 11/2013 | Walters et al. |
| 8,597,170 | B2 | 12/2013 | Walters et al. |
| 8,684,904 | B2 | 4/2014 | Campbell et al. |
| 8,721,517 | B2 | 5/2014 | Zeng et al. |
| 8,992,163 | B2 | 3/2015 | McBride et al. |
| 9,072,825 | B2 | 7/2015 | Pfeffer et al. |
| 9,138,518 | B2 | 9/2015 | Yuen et al. |
| 9,162,017 | B2 | 10/2015 | Evans et al. |
| 9,308,302 | B2 | 4/2016 | Zeng |
| 9,308,304 | B2 | 4/2016 | Peters et al. |
| 9,327,067 | B2 | 5/2016 | Zeng et al. |
| 9,364,592 | B2 | 6/2016 | McBride et al. |
| 9,364,593 | B2 | 6/2016 | McBride et al. |
| 9,381,288 | B2 | 7/2016 | Schenck et al. |
| 9,421,311 | B2 | 8/2016 | Tanner et al. |
| 9,446,179 | B2 | 9/2016 | Keenan et al. |
| 9,474,840 | B2 | 10/2016 | Siess |
| 9,669,142 | B2 | 6/2017 | Spanier et al. |
| 9,675,740 | B2 | 6/2017 | Zeng et al. |
| 9,717,833 | B2 | 8/2017 | McBride et al. |
| 9,770,543 | B2 | 9/2017 | Tanner et al. |
| 9,872,947 | B2 | 1/2018 | Keenan et al. |
| 9,895,476 | B2 | 2/2018 | Larose et al. |
| 9,907,890 | B2 | 3/2018 | Muller |
| 9,956,332 | B2 | 5/2018 | Larose et al. |
| 9,962,475 | B2 | 5/2018 | Yuen et al. |
| 9,964,115 | B2 | 5/2018 | Scheckel |
| 10,029,037 | B2 | 7/2018 | Muller et al. |
| 10,039,872 | B2 | 8/2018 | Zeng et al. |
| 10,071,192 | B2 | 9/2018 | Zeng |
| 10,086,121 | B2 | 10/2018 | Fitzgerald et al. |
| 10,105,475 | B2 | 10/2018 | Muller |
| 10,117,980 | B2 | 11/2018 | Keenan et al. |
| 10,149,932 | B2 | 12/2018 | McBride et al. |
| 10,215,187 | B2 | 2/2019 | McBride et al. |
| 10,232,099 | B2 | 3/2019 | Peters et al. |
| 10,251,985 | B2 | 4/2019 | Larose et al. |
| 10,251,986 | B2 | 4/2019 | Larose et al. |
| 10,478,539 | B2 | 11/2019 | Pfeffer et al. |
| 10,478,540 | B2 | 11/2019 | Scheckel et al. |
| 10,525,178 | B2 | 1/2020 | Zeng |
| 10,576,192 | B2 | 3/2020 | Muller et al. |
| 10,576,193 | B2 | 3/2020 | Tanner et al. |
| 10,709,829 | B2 | 7/2020 | Muller |
| 10,709,830 | B2 | 7/2020 | Tanner et al. |
| 10,765,789 | B2 | 9/2020 | Zeng et al. |
| 10,765,791 | B2 | 9/2020 | Moyer et al. |
| 10,780,208 | B2 | 9/2020 | Siess et al. |
| 10,786,610 | B2 | 9/2020 | Zeng |
| 10,799,624 | B2 | 10/2020 | Pfeffer et al. |
| 10,842,921 | B2 | 11/2020 | Siess et al. |
| 10,864,308 | B2 | 12/2020 | Muller et al. |
| 10,864,309 | B2 | 12/2020 | McBride et al. |
| 10,874,783 | B2 | 12/2020 | Pfeffer et al. |
| 10,894,115 | B2 | 1/2021 | Pfeffer et al. |
| 10,918,774 | B2 | 2/2021 | Stanfield et al. |
| 10,960,116 | B2 | 3/2021 | Yuen et al. |
| 10,960,118 | B2 | 3/2021 | Sunagawa |
| 10,980,927 | B2 | 4/2021 | Pfeffer et al. |
| 11,027,114 | B2 | 6/2021 | D'Amrosio et al. |
| 11,033,727 | B2 | 6/2021 | Tuval et al. |
| 11,058,865 | B2 | 7/2021 | Fitzgerald et al. |
| 11,123,539 | B2 | 9/2021 | Pfeffer et al. |
| 11,129,978 | B2 | 9/2021 | Pfeffer et al. |
| 11,167,124 | B2 | 11/2021 | Pfeffer et al. |
| 11,185,677 | B2 | 11/2021 | Salahieh et al. |
| 11,229,786 | B2 | 1/2022 | Zeng et al. |
| 11,235,138 | B2 | 2/2022 | Gross-Hardt et al. |
| 11,253,693 | B2 | 2/2022 | Pfeffer et al. |
| 11,260,213 | B2 | 3/2022 | Zeng et al. |
| 11,273,301 | B2 | 3/2022 | Pfeffer et al. |
| 11,311,712 | B2 | 4/2022 | Zeng et al. |
| 11,338,124 | B2 | 5/2022 | Pfeffer et al. |
| 11,357,967 | B2 | 6/2022 | Zeng et al. |
| 11,400,276 | B2 | 8/2022 | Chopra et al. |
| 11,497,896 | B2 | 11/2022 | Tanner et al. |
| 11,517,736 | B2 | 12/2022 | Earles et al. |
| 11,529,062 | B2 | 12/2022 | Moyer et al. |
| 11,583,659 | B2 | 2/2023 | Pfeffer et al. |
| 11,628,294 | B2 | 4/2023 | Chopra et al. |
| 11,708,833 | B2 | 7/2023 | McBride et al. |
| 11,754,075 | B2 | 9/2023 | Schuelke et al. |
| 11,786,700 | B2 | 10/2023 | Pfeffer et al. |
| 2004/0191116 | A1 | 9/2004 | Jarvik et al. |
| 2005/0267322 | A1 | 12/2005 | LaRose |
| 2008/0114339 | A1 | 5/2008 | McBride et al. |
| 2009/0060743 | A1 | 3/2009 | McBride et al. |
| 2010/0234698 | A1 | 9/2010 | Manstrom et al. |
| 2014/0024950 | A1 * | 1/2014 | Hiltner ................. A61B 5/6851 600/478 |
| 2017/0055908 | A1 | 3/2017 | Radman et al. |
| 2017/0056620 | A1 | 3/2017 | Farnan |
| 2017/0128646 | A1 | 5/2017 | Karch |
| 2017/0296725 | A1 | 10/2017 | Peters et al. |
| 2018/0303990 | A1 | 10/2018 | Siess et al. |
| 2018/0311423 | A1 | 11/2018 | Zeng et al. |
| 2019/0053714 | A1 | 2/2019 | Guelen et al. |
| 2019/0076167 | A1 | 3/2019 | Fantuzzi et al. |
| 2019/0247627 | A1 | 8/2019 | Korkuch et al. |
| 2020/0030510 | A1 | 1/2020 | Higgins |
| 2020/0330667 | A1 | 10/2020 | Fantuzzi et al. |
| 2020/0360663 | A1 | 11/2020 | Smith et al. |
| 2021/0015982 | A1 | 1/2021 | Kerkhoffs et al. |
| 2021/0038785 | A1 | 2/2021 | Siess et al. |
| 2021/0069392 | A1 | 3/2021 | Muller et al. |
| 2021/0106810 | A1 | 4/2021 | Pfeffer et al. |
| 2021/0170081 | A1 | 6/2021 | Kanz |
| 2021/0275794 | A1 | 9/2021 | Sunagawa |
| 2021/0290164 | A1 | 9/2021 | Linder et al. |
| 2021/0322757 | A1 | 10/2021 | D'Ambrosio et al. |
| 2022/0134082 | A1 | 5/2022 | Pfeffer et al. |
| 2022/0167862 | A1 | 6/2022 | Edelman et al. |
| 2023/0149696 | A1 | 5/2023 | Logan et al. |
| 2023/0149699 | A1 | 5/2023 | Beekman et al. |
| 2024/0325721 | A1 * | 10/2024 | Beekman ............ A61M 60/419 |

FOREIGN PATENT DOCUMENTS

| | | | |
|---|---|---|---|
| EP | 3508116 | A1 | 7/2019 |
| EP | 3352808 | B1 | 9/2023 |
| JP | 2015527917 | A | 9/2015 |
| JP | 2021532884 | A | 12/2021 |
| WO | 2011039091 | A1 | 4/2011 |
| WO | 2014043650 | A2 | 3/2014 |
| WO | 2018096531 | A1 | 5/2018 |
| WO | 2022140635 | A1 | 6/2022 |

OTHER PUBLICATIONS

International Search Report and Written Opinion for International Application No. PCT/US2023/027791, dated Oct. 10, 2023.

* cited by examiner

PERCUTANEOUS CIRCULATORY SUPPORT DEVICE INCLUDING PROXIMAL PRESSURE SENSOR

CROSS-REFERENCE TO RELATED APPLICATIONS

This application claims priority to U.S. Provisional Application No. 63/390,054, filed Jul. 18, 2022, which is herein incorporated by reference in its entirety.

TECHNICAL FIELD

The present disclosure relates to percutaneous circulatory support systems. More specifically, the disclosure relates to percutaneous circulatory support devices that include one or more pressure sensors.

BACKGROUND

Percutaneous circulatory support devices can provide transient support for up to approximately several weeks in patients with compromised heart function or cardiac output. Some percutaneous circulatory support devices include one or more pressure sensors for measuring intravascular pressures. Measuring these pressures facilitates, for example, (1) detecting unintended device position changes within the heart, and (2) determining cardiac output, which in turn facilitates evaluation of potential treatment changes. However, devices including pressure sensors may have several drawbacks. For example, the pressure sensors can be damaged during deployment. As another example, the sensed pressures may be inaccurate due to the operating speed of the device and other dynamic pressure effects. Accordingly, there is a need for improved devices that include pressure sensors.

SUMMARY

In an Example 1, a percutaneous circulatory support device includes a housing and an impeller disposed within the housing. The impeller is configured to rotate relative to the housing to cause blood to flow through the housing. A motor is operably coupled to the impeller, and the motor is configured to rotate the impeller relative to the housing. A catheter is coupled to the motor. A collar is coupled to catheter and disposed proximally relative to the housing. The collar includes an internal chamber, and a pressure sensor is disposed within the internal chamber of the collar.

In an Example 2, the percutaneous circulatory support device of Example 1, wherein the collar further includes an aperture coupled to the internal chamber.

In an Example 3, the percutaneous circulatory support device of Example 2, wherein the aperture is a distally-facing aperture.

In an Example 4, the percutaneous circulatory support device of any of Examples 2-3, wherein the collar further includes an outer surface, the outer surface including a tapering distal portion forming the aperture.

In an Example 5, the percutaneous circulatory support device of Example 4, wherein the outer surface further includes a tapering proximal portion.

In an Example 6, the percutaneous circulatory support device of Example 5, wherein the tapering distal portion has a first slope, the tapering proximal portion has a second slope, and the first slope is greater than the second slope.

In an Example 7, the percutaneous circulatory support device of any of Examples 5-6, wherein the outer surface further includes a cylindrical surface between the tapering distal portion and the tapering proximal portion.

In an Example 8, the percutaneous circulatory support device of Example 2, wherein the aperture is a transversely-facing aperture.

In an Example 9, the percutaneous circulatory support device of Example 8, wherein the collar further includes a distally-facing aperture coupled to the internal chamber.

In an Example 10, the percutaneous circulatory support device of any of Examples 8-9, wherein the transversely-facing aperture is a first transversely-facing aperture, and the collar further includes a second transversely-facing aperture coupled to the internal chamber.

In an Example 11, the percutaneous circulatory support device of Example 2, wherein the aperture extends at an acute angle relative to a longitudinal axis of the internal chamber.

In an Example 12, the percutaneous circulatory support device of any of Examples 1-11, further including a sensor mount disposed within the internal chamber of the collar and coupled to the pressure sensor.

In an Example 13, a percutaneous circulatory support device includes a housing and an impeller disposed within the housing. The impeller is configured to rotate relative to the housing to cause blood to flow through the housing. A motor is operably coupled to the impeller, and the motor is configured to rotate the impeller relative to the housing. A catheter is coupled to the motor, and a collar is coupled to catheter and disposed proximally relative to the housing. The collar includes an internal chamber, a distally-facing aperture coupled to the internal chamber, and a proximally-facing aperture coupled to the internal chamber. A pressure sensor is disposed within the internal chamber of the collar. A sensor cable is coupled to the pressure sensor, and the sensor cable extends through the proximally-facing aperture.

In an Example 14, the percutaneous circulatory support device of Example 13, wherein the pressure sensor includes one of an optical pressure sensor and an electrical pressure sensor.

In an Example 15, the percutaneous circulatory support device of any of Examples 13-14, wherein the pressure sensor is disposed apart from an outer surface of the catheter by at least 0.001 inches.

In an Example 16, a percutaneous circulatory support device includes a housing having an inlet and an outlet. An impeller is disposed within the housing, and the impeller is configured to rotate relative to the housing to cause blood to flow into the inlet, through the housing, and out of the outlet. A motor is operably coupled to the impeller, and the motor is configured to rotate the impeller relative to the housing. A catheter is coupled to the motor. A collar is coupled to the catheter and is disposed proximally relative to the housing, and the collar includes an internal chamber. A pressure sensor is disposed within the internal chamber of the collar.

In an Example 17, the percutaneous circulatory support device of Example 16, wherein the collar further includes an aperture coupled to the internal chamber.

In an Example 18, the percutaneous circulatory support device of Example 17, wherein the aperture is a distally-facing aperture.

In an Example 19, the percutaneous circulatory support device of Example 18, wherein the collar further includes an outer surface, the outer surface including a tapering distal portion forming the distally-facing aperture.

In an Example 20, the percutaneous circulatory support device of Example 17, wherein the aperture is a transversely-facing aperture.

In an Example 21, the percutaneous circulatory support device of Example 20, wherein the collar further includes a distally-facing aperture coupled to the internal chamber.

In an Example 22, the percutaneous circulatory support device of Example 20, wherein the transversely-facing aperture is a first transversely-facing aperture, and the collar further includes a second transversely-facing aperture coupled to the internal chamber.

In an Example 23, the percutaneous circulatory support device of Example 17, wherein the aperture extends at an acute angle relative to a longitudinal axis of the internal chamber.

In an Example 24, the percutaneous circulatory support device of Example 17, further including a sensor mount disposed within the internal chamber of the collar and coupled to the pressure sensor.

In an Example 25, the percutaneous circulatory support device of Example 24, wherein the pressure sensor is adhered to the sensor mount.

In an Example 26, the percutaneous circulatory support device of Example 17, further including a sensor cable coupled to the pressure sensor.

In an Example 27, the percutaneous circulatory support device of Example 17, wherein the collar further includes a proximally-facing aperture coupled to the internal chamber, the sensor cable extending through the proximally-facing aperture.

In an Example 28, the percutaneous circulatory support device of Example 27, wherein the collar further includes an outer surface, the outer surface including a tapering proximal portion forming the proximally-facing aperture.

In an Example 29, the percutaneous circulatory support device of Example 17, wherein the collar further includes an outer surface, the outer surface including a tapering distal portion and a tapering proximal portion.

In an Example 30, the percutaneous circulatory support device of Example 29, wherein the tapering distal portion has a first slope, the tapering proximal portion has a second slope, and the first slope is greater than the second slope.

In an Example 31, the percutaneous circulatory support device of Example 17, wherein the pressure sensor includes one of an optical pressure sensor and an electrical pressure sensor.

In an Example 32, A percutaneous circulatory support device includes a housing including an inlet and an outlet. An impeller is disposed within the housing, and the impeller is configured to rotate relative to the housing to cause blood to flow into the inlet, through the housing, and out of the outlet. A motor is operably coupled to the impeller, and the motor is configured to rotate the impeller relative to the housing. A catheter is coupled to the motor. A collar is coupled to the catheter and is disposed proximally relative to the housing. The collar includes an internal chamber, a distally-facing aperture coupled to the internal chamber, and a proximally-facing aperture coupled to the internal chamber. A pressure sensor is disposed within the internal chamber of the collar. A sensor cable is coupled to the pressure sensor, and the sensor cable extends through the proximally-facing aperture.

In an Example 33, the percutaneous circulatory support device of Example 32, wherein the pressure sensor is disposed apart from an outer surface of the catheter by at least 0.001 inches.

In an Example 34, a method of manufacturing a percutaneous circulatory support device includes: positioning an impeller within a housing such that the impeller is rotatable relative to the housing; operably coupling a motor to the impeller; coupling a catheter to the motor; coupling a pressure sensor to a collar; and thereafter coupling the collar and the pressure sensor to the catheter proximally of the motor.

In an Example 35, the method of Example 34, wherein coupling the collar and the pressure sensor to the catheter includes distally advancing the collar and the pressure sensor along the catheter.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
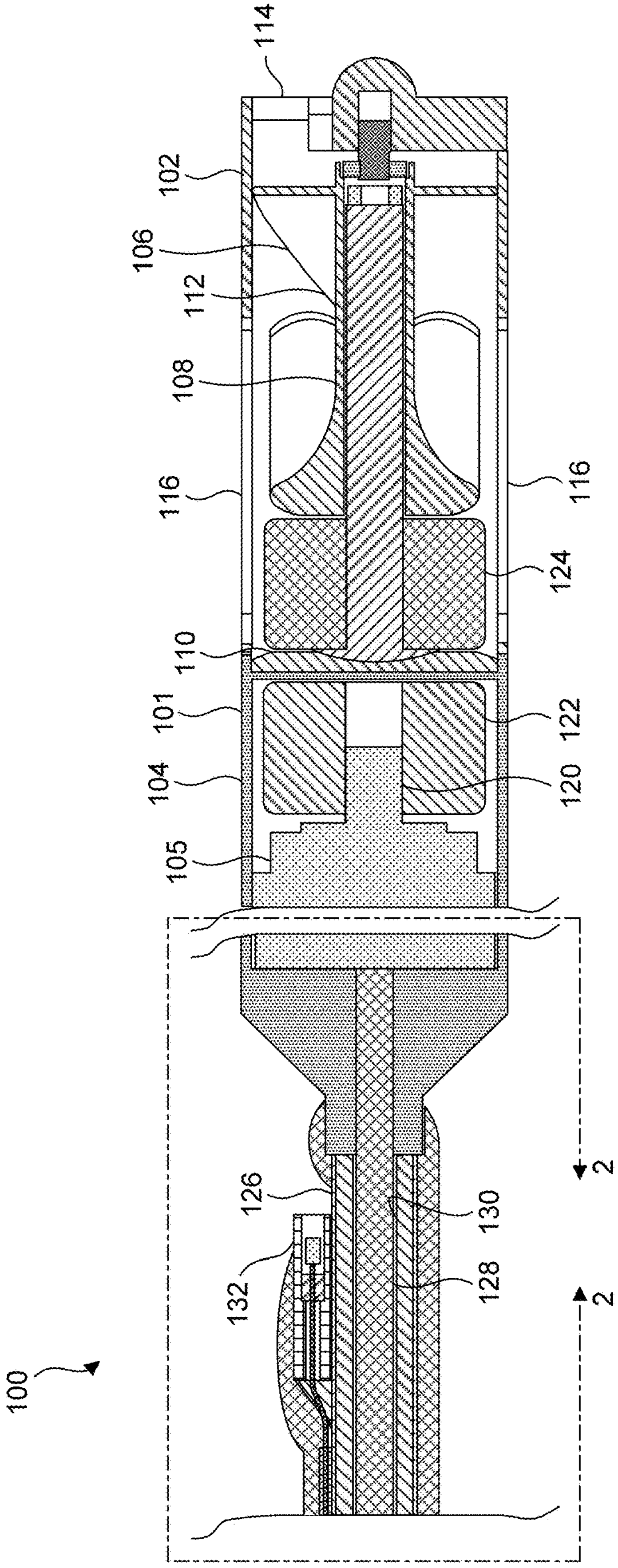
FIG. 1 is a side sectional view of an illustrative percutaneous circulatory support device (also referred to herein, interchangeably, as a "blood pump"), in accordance with embodiments of the subject matter disclosed herein.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 depicts a partial side sectional view of an illustrative percutaneous circulatory support device 100 (also referred to herein, interchangeably, as a "blood pump") in accordance with embodiments of the subject matter disclosed herein. The device 100 may form part of a percutaneous circulatory support system, together with a guidewire and an introducer sheath (not shown). More specifically, the guidewire and the introducer sheath may facilitate percutaneously delivering the device 100 to a target location within a patient, such as within the patient's heart. Alternatively, the device 100 may be delivered to a different target location within a patient.

With continued reference to FIG. 1, the device 100 generally includes a housing 101 that includes an impeller housing 102 and a motor housing 104. In some embodiments, the impeller housing 102 and the motor housing 104 may be integrally or monolithically constructed. In other embodiments, the impeller housing 102 and the motor housing 104 may be separate components configured to be removably or permanently coupled. In some embodiments, the blood pump 100 may lack a separate motor housing 104 and the impeller housing 102 may be coupled directly to the motor 105 described below, or the motor housing 104 may be integrally constructed with the motor 105 described below.

The impeller housing 102 carries an impeller assembly 106 therein. The impeller assembly 106 includes an impeller shaft 108 that is rotatably supported by at least one bearing, such as a bearing 110. The impeller assembly 106 also includes an impeller 112 that rotates relative to the impeller housing 102 to drive blood through the device 100. More specifically, the impeller 112 causes blood to flow from a blood inlet 114 (FIG. 1) formed on the impeller housing 102, through the impeller housing 102, and out of a blood outlet 116 formed on the impeller housing 102. In some embodiments and as illustrated, the impeller shaft 108 and the impeller 112 may be separate components, and in other embodiments the impeller shaft 108 and the impeller 112 may be integrated. In some embodiments and as illustrated, the inlet 114 and/or the outlet 116 may each include multiple apertures. In other embodiments, the inlet 114 and/or the outlet 116 may each include a single aperture. In some embodiments and as illustrated, the inlet 114 may be formed on an end portion of the impeller housing 102 and the outlet 116 may be formed on a side portion of the impeller housing 102. In other embodiments, the inlet 114 and/or the outlet 116 may be formed on other portions of the impeller housing 102. In some embodiments, the impeller housing 102 may couple to a distally extending cannula (not shown), and the cannula may receive and deliver blood to the inlet 114.

With continued reference to FIG. 1, the motor housing 104 carries a motor 105, and the motor 105 is configured to rotatably drive the impeller 112 relative to the impeller housing 102. In the illustrated embodiment, the motor 105 rotates a drive shaft 120, which is coupled to a driving magnet 122. Rotation of the driving magnet 122 causes rotation of a driven magnet 124, which is connected to and rotates together with the impeller assembly 106. More specifically, in embodiments incorporating the impeller shaft 108, the impeller shaft 108 and the impeller 112 are configured to rotate with the driven magnet 124. In other embodiments, the motor 105 may couple to the impeller assembly 106 via other components.

In some embodiments, a controller (not shown) may be operably coupled to the motor 105 and configured to control the motor 105. In some embodiments, the controller may be disposed within the motor housing 104. In other embodiments, the controller may be disposed outside of the motor housing 104 (for example, in an independent housing, etc.). In some embodiments, the controller may include multiple components, one or more of which may be disposed within the motor housing 104. According to embodiments, the controller may be, may include, or may be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more Central Processing Units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like. In other embodiments, the motor 105 may be controlled in other manners.

Figure 2:
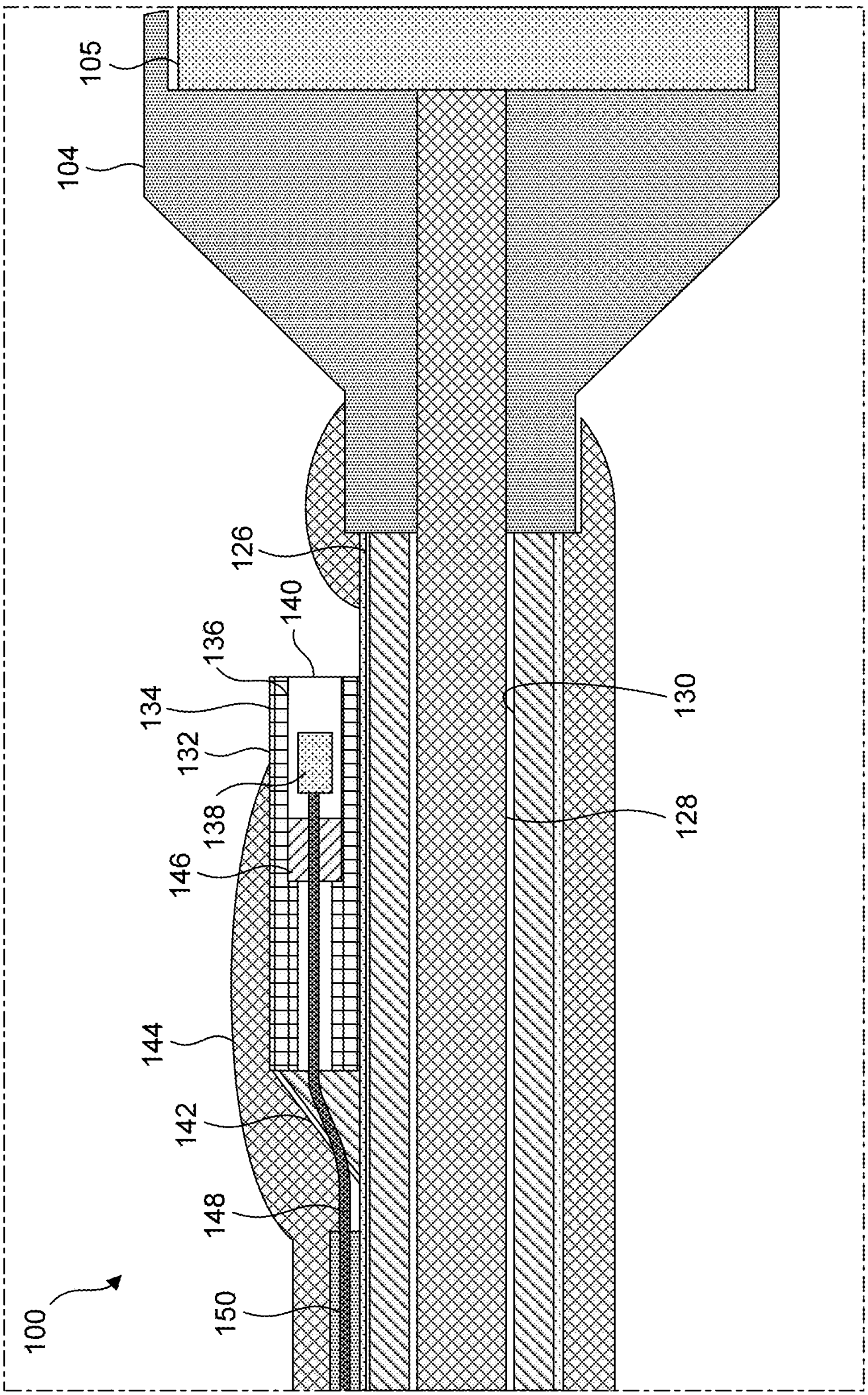
FIG. 2 is a detail view of the illustrative percutaneous circulatory support device within line 2-2 of FIG. 1.

With continued reference to FIG. 1 and additional reference to FIG. 2, the motor housing 104 couples to a catheter 126 opposite the impeller housing 102. The catheter 126 may couple to the motor housing 104 in various manners, such as laser welding, soldering, adhesive bonding, thermal polymer reflowing, or the like. The catheter 126 extends proximally away from the motor housing 104. The catheter 126 carries a motor cable 128 within a main lumen 130, and the motor cable 128 may operably couple the motor 105 to the controller (not shown) and/or an external power source (not shown). Externally, the catheter 126 carries a sensor assembly 132 for measuring pressure within the vasculature of a patient, for example, within the aorta. Advantageously, the sensor assembly 132 is positioned, relative to the other components of the device 100, in location for obtaining highly accurate pressure data. For example, the proximal position of the sensor assembly 132 relative to the motor housing 104 and the motor 105 reduces or eliminates the motor speed-related or dynamic pressure-related sensing inaccuracies. Such inaccuracies are typical of other percutaneous circulatory support devices that employ pressure sensors located more distally relative to the motor or impeller assembly, for example, devices that employ pressure sensors located near the outlet.

With specific reference to FIG. 2, the sensor assembly 132 includes a sensor housing 134 having a counterbore-shaped internal chamber 136. A pressure sensor 138, such as an optical or electrical pressure sensor, is disposed within the internal chamber 136. As such, the sensor housing 134 protects the pressure sensor 138 during deployment of the device 100. The sensor housing 134 also includes a distally-facing aperture 140 coupled to the internal chamber 136. The aperture 140 permits blood to enter the internal chamber 136, and the aperture 140 thereby permits the pressure sensor 138 to sense the pressure of the blood.

The sensor housing 134 may take various forms. For example, the sensor housing 134 may be a tube or ferrule manufactured from, for example, one or more metals, one or more plastics, composites, or the like. The sensor housing 134 may be coupled to the catheter 126 via one or more weldments (not shown), one or more adhesives 142, and/or an outer jacket 144 surrounding the sensor housing 134 and the catheter 126. The sensor housing 134 may also include a sensor mount 146 within the internal chamber 136. The sensor mount 146 facilitates supporting the pressure sensor 138 apart from the walls of the sensor housing 134 (that is, the sensor mount 146 centers the pressure sensor 138 within the internal chamber 136), which in turn facilitates high-accuracy pressure sensing.

With continued reference to FIG. 2, the sensor assembly 132 further includes a sensor cable 148 coupled to the pressure sensor 138. The sensor cable 148 may operably couple the pressure sensor to the controller (not shown). As illustrated, the sensor cable 148 may extend through the sensor mount 146 and support the pressure sensor 138 apart from the walls of the sensor housing 134. The sensor cable 148 extends proximally, through the adhesive 142, and through a cable lumen 150 coupled to the catheter 126. The cable lumen 150 may be coupled to the catheter 126 via one or more weldments (not shown), an adhesive (not shown), and/or the outer jacket 144. In other embodiments, the cable lumen 150 may be omitted, and the sensor cable 148 may extend through the main lumen 130 of the catheter 126 or lie directly under the outer jacket 144.

Figure 3:
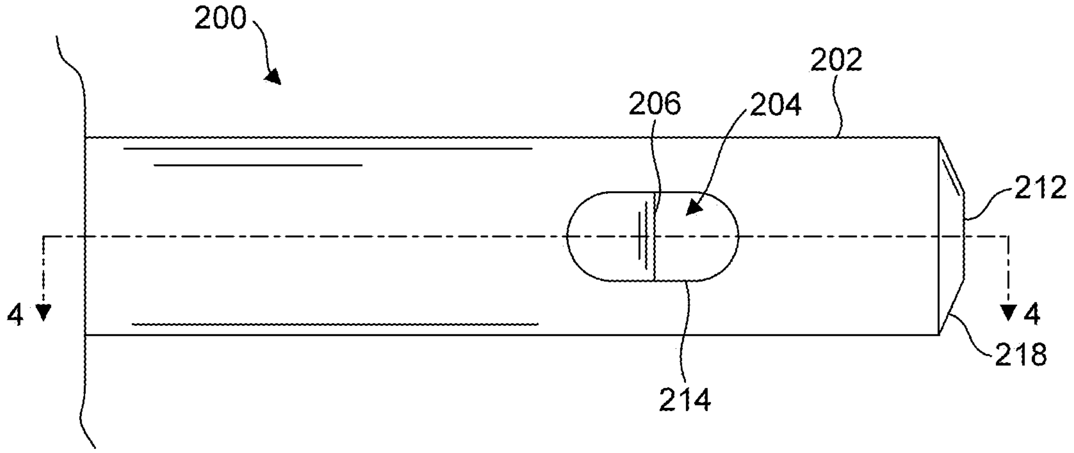
FIG. 3 is a side view of an illustrative sensor assembly of a percutaneous circulatory support device, in accordance with embodiments of the subject matter disclosed herein.
Figure 4:
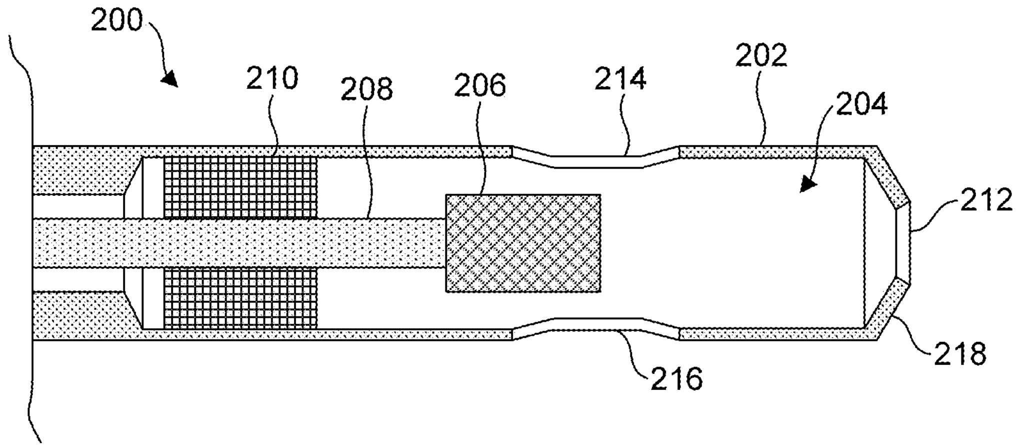
FIG. 4 is a side sectional view of the sensor assembly along line 4-4 of FIG. 3.

FIGS. 3 and 4 depict another sensor assembly 200 in accordance with embodiments of the subject matter disclosed herein. The sensor assembly 200 may be used as part of the percutaneous circulatory support device 100 in place of the sensor assembly 132 described above. The sensor assembly 200 is similar to the sensor assembly 132 described above. More specifically, the sensor assembly 200 includes a sensor housing 202 that has an internal chamber 204, a pressure sensor 206, a sensor cable 208 (FIG. 4), and an optional sensor mount 210 (FIG. 4) which is disposed within the internal chamber 204. The sensor housing 202 also includes a plurality of apertures coupled to the internal chamber 204. More specifically, the sensor housing 202 includes a distally-facing aperture 212, a first transversely-facing aperture 214, and a second transversely-facing aperture 216 (FIG. 4). The plurality of apertures facilitate blood flow through the sensor housing 202 and thereby reduce thrombi formation. Alternatively, the sensor housing 202 could include a different number of apertures. For example, the sensor housing 202 could include one or more transversely-facing apertures and omit a distally-facing aperture. In any case, each of the apertures may be sized to inhibit the sensor 206 from passing therethrough, for example, if the sensor 206 detaches from the sensor cable 208 in use. The apertures may also have an oval shape, as shown in FIG. 3, or various other shapes.

In some embodiments and as illustrated in FIGS. 3 and 4, the distally-facing aperture 212 is formed by a tapering portion 218 of the sensor housing 202. The tapering portion 218 may be formed by crimping or coupling a separate piece of material to the remainder of the sensor housing 202. In other embodiments, the distally-facing aperture 212 can be a flat feature perpendicular to the axis of the internal chamber 204. In other embodiments, the tapering portion 218 may be created via a counterbore drilling process from the proximal end of the sensor housing 202.

In some embodiments and as illustrated in FIGS. 3 and 4, the sensor 206 is at least partially aligned with the first transversely-facing aperture 214 and the second transversely-facing aperture 216. This position of the sensor 206 provides relatively little space within sensor housing 202 in which bubbles could form, which could reduce sensing accuracy. Alternatively, the sensor 206 may be disposed in other positions within the sensor housing 202. In some embodiments, the sensor 206 includes a surface energy-reducing coating (not shown), such as silicone, to inhibit bubble formation on the sensor 206 or within the sensor housing 202.

Figure 5:
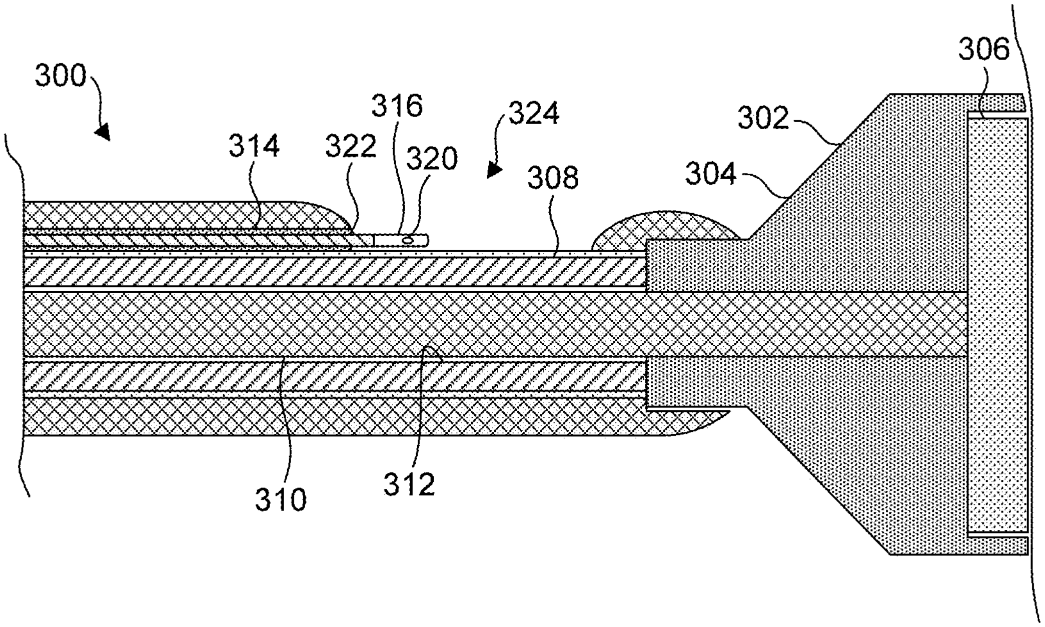
FIG. 5 is a side sectional view of an illustrative percutaneous circulatory support system, in accordance with embodiments of the subject matter disclosed herein.
Figure 6:
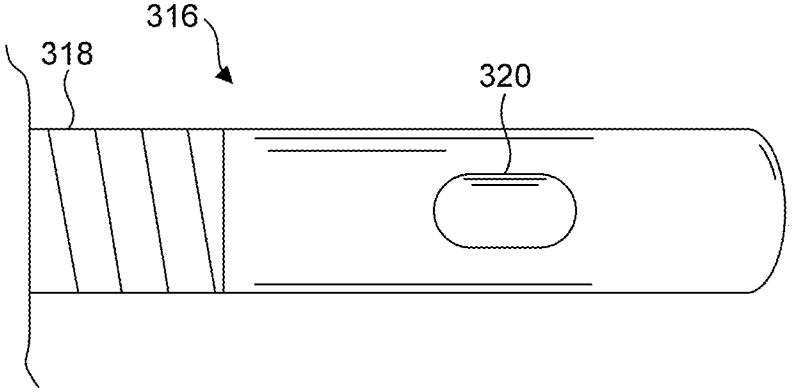
FIG. 6 is a side view of a pressure-sensing guidewire of the percutaneous circulatory support system of FIG. 5.

FIG. 5 depicts a partial side sectional view of an illustrative percutaneous circulatory support system 300 in accordance with embodiments of the subject matter disclosed herein. The system 300 includes a percutaneous circulatory support device 302 that is similar to the device 100 described above. More specifically, a distal portion (not shown) of the device 302 generally includes an impeller housing and an impeller, such as the impeller housing 102 and the impeller 112, respectively, described above and shown elsewhere. A proximal portion of the device 302 includes a motor housing 304 that carries a motor 306, and the motor housing 304 couples to a catheter 308 opposite the motor 306. The catheter 308 extends proximally away from the motor housing 304. The catheter 308 carries a motor cable 310 within a main lumen 312, and the motor cable 310 may operably couple the motor 306 to a controller (not shown) and/or an external power source (not shown). Externally, the catheter 308 carries a guidewire lumen 314 that receives a pressure-sensing guidewire 316. The pressure-sensing guidewire 316 may operably couple to the controller, and the guidewire 316 may take various specific forms. However, and with additional reference to FIG. 6, the pressure-sensing guidewire 316 generally includes an elongated flexible body 318 that carries a pressure sensor 320, such as an optical or electrical pressure sensor. The pressure-sensing guidewire 316 is advanced from a proximal end (not shown) of the guidewire lumen 314 to a distal end 322 of the guidewire lumen 314 (either before or after the device 302 is positioned in the vasculature of the patient). The sensor 320 extends distally from the guidewire lumen 314 and is positioned in a sensing region 324 of the catheter 308. The sensing region 324 is located proximally from the motor housing 304 and the motor 306, which, as described above, facilitates for obtaining highly accurate pressure data. The guidewire 316 may additionally or alternatively sense pressure at various other locations relative to the catheter 308.

In other embodiments, the system 300 may take other forms or include additional components. For example, the device 302 may include a sensor housing, such as the sensor housing 134 or the sensor housing 202 described above and shown elsewhere, for receiving and protecting the pressure sensor 320 of the guidewire 316. Such a sensor housing may be coupled to the catheter 308 in various manners, including those described above in connection with the catheter 126 and the sensor housing 134 or the sensor housing 202. As another example, the guidewire 316 may be fixed relative to the catheter 126.

A method of manufacturing the percutaneous circulatory support device 100 may be as follows, and a method of manufacturing the device 302 may be similar. The impeller 112 is positioned within the impeller housing 102 such that the impeller 112 is rotatable relative to the impeller housing 102. The impeller 112 is operably coupled to the motor 105, and the catheter 126 is positioned adjacent to the motor housing 104. The cable lumen 150 is positioned adjacent to the catheter 126 and coupled to the catheter 126 via a process which may include forming the outer jacket 144 via at least one polymer reflow process. The pressure sensor 138 and the sensor cable 148 are then coupled to the sensor housing 134 such that the sensor 138 is positioned within the internal chamber 136 of the sensor housing 134. The sensor cable 148 is positioned in the cable lumen 150 and the sensor housing 134 and the pressure sensor within 138 are positioned adjacent to the catheter 126. The sensor housing 134 and the pressure sensor 138 within the sensor housing 134 are coupled to the catheter 126, for example, via one or more of welding, adhering, and covering the above components with the outer jacket 144. Covering these components with the outer jacket 144 may include forming the outer jacket 144 via a polymer reflow process.

Figure 7:
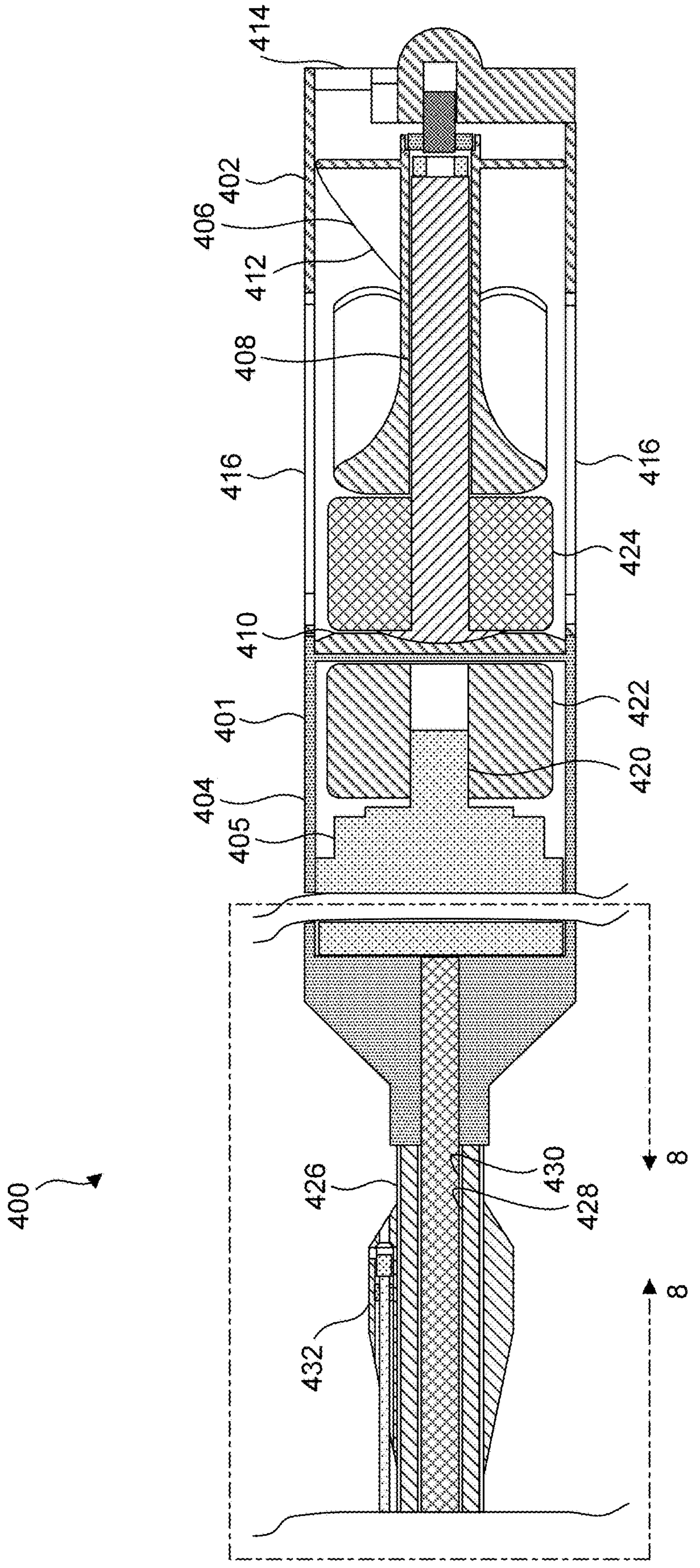
FIG. 7 is a side sectional view of another illustrative percutaneous circulatory support device, in accordance with embodiments of the subject matter disclosed herein.

FIG. 7 depicts a partial side sectional view of an illustrative percutaneous circulatory support device 400 (also referred to herein, interchangeably, as a "blood pump") in accordance with embodiments of the subject matter disclosed herein. The device 400 may form part of a percutaneous circulatory support system, together with a guidewire and an introducer sheath (not shown). More specifically, the guidewire and the introducer sheath may facilitate percutaneously delivering the device 400 to a target location within a patient, such as within the patient's heart. Alternatively, the device 400 may be delivered to a different target location within a patient.

With continued reference to FIG. 7, the device 400 generally includes a housing 401 that includes an impeller housing 402 and a motor housing 404. In some embodiments, the impeller housing 402 and the motor housing 404 may be integrally or monolithically constructed. In other embodiments, the impeller housing 402 and the motor housing 404 may be separate components configured to be removably or permanently coupled. In some embodiments, the blood pump 400 may lack a separate motor housing 404 and the impeller housing 402 may be coupled directly to the motor 405 described below, or the motor housing 404 may be integrally constructed with the motor 405 described below.

The impeller housing 402 carries an impeller assembly 406 therein. The impeller assembly 406 includes an impeller shaft 408 that is rotatably supported by at least one bearing, such as a bearing 410. The impeller assembly 406 also includes an impeller 412 that rotates relative to the impeller housing 402 to drive blood through the device 400. More specifically, the impeller 412 causes blood to flow from a blood inlet 414 (FIG. 7) formed on the impeller housing 402, through the impeller housing 402, and out of a blood outlet 416 formed on the impeller housing 402. In some embodiments and as illustrated, the impeller shaft 408 and the impeller 412 may be separate components, and in other embodiments the impeller shaft 408 and the impeller 412 may be integrated. In some embodiments and as illustrated, the inlet 414 and/or the outlet 416 may each include multiple apertures. In other embodiments, the inlet 414 and/or the outlet 416 may each include a single aperture. In some embodiments and as illustrated, the inlet 414 may be formed on an end portion of the impeller housing 402 and the outlet 416 may be formed on a side portion of the impeller housing 402. In other embodiments, the inlet 414 and/or the outlet 416 may be formed on other portions of the impeller housing 402. In some embodiments, the impeller housing 402 may couple to a distally extending cannula (not shown), and the cannula may receive and deliver blood to the inlet 414.

With continued reference to FIG. 7, the motor housing 404 carries a motor 405, and the motor 405 is configured to rotatably drive the impeller 412 relative to the impeller housing 402. In the illustrated embodiment, the motor 405 rotates a drive shaft 420, which is coupled to a driving magnet 422. Rotation of the driving magnet 422 causes rotation of a driven magnet 424, which is connected to and rotates together with the impeller assembly 406. More specifically, in embodiments incorporating the impeller shaft 408, the impeller shaft 408 and the impeller 412 are configured to rotate with the driven magnet 424. In other embodiments, the motor 405 may couple to the impeller assembly 406 via other components.

In some embodiments, a controller (not shown) may be operably coupled to the motor 405 and configured to control the motor 405. In some embodiments, the controller may be disposed within the motor housing 404. In other embodiments, the controller may be disposed outside of the motor housing 404 (for example, in an independent housing, etc.). In some embodiments, the controller may include multiple components, one or more of which may be disposed within the motor housing 404. According to embodiments, the controller may be, may include, or may be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more Central Processing Units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like. In other embodiments, the motor 405 may be controlled in other manners.

Figure 8:
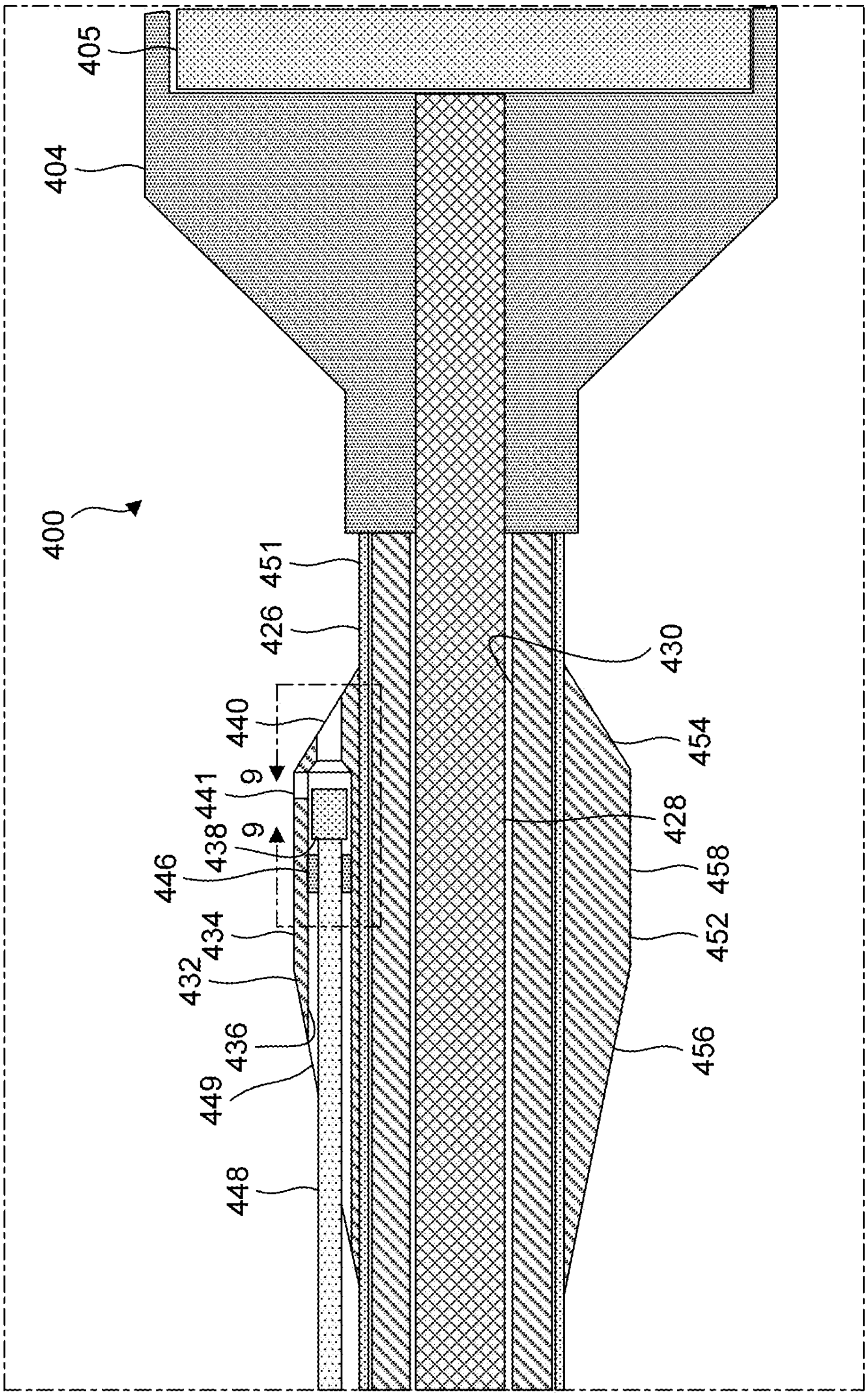
FIG. 8 is a detail view of the illustrative percutaneous circulatory support device within line 8-8 of FIG. 7.

With continued reference to FIG. 7 and additional reference to FIG. 8, the motor housing 404 couples to a catheter 426 opposite the impeller housing 402. The catheter 426 may couple to the motor housing 404 in various manners, such as laser welding, soldering, or the like. The catheter 426 extends proximally away from the motor housing 404. The catheter 426 carries a motor cable 428 within a main lumen 430, and the motor cable 428 may operably couple the motor 405 to the controller (not shown) and/or an external power source (not shown). Externally, the catheter 426 carries a sensor assembly 432 for measuring pressure within the vasculature of a patient, for example, within the aorta. Advantageously, the sensor assembly 432 is positioned, relative to the other components of the device 400, in location for obtaining highly accurate pressure data. For example, the proximal position of the sensor assembly 432 relative to the motor housing 404 and the motor 405 reduces or eliminates the motor speed-related or dynamic pressure-related sensing inaccuracies. Such inaccuracies are typical of other percutaneous circulatory support devices that employ pressure sensors located more distally relative to the motor or impeller assembly, for example, devices that employ pressure sensors located near the outlet.

With specific reference to FIG. 8, the sensor assembly 432 includes a collar 434 having a counterbore-shaped internal chamber 436. A pressure sensor 438, such as an optical or electrical pressure sensor, is disposed within the internal chamber 436. As such, the collar 434 protects the pressure sensor 438 during deployment of the device 400. The collar 434 also includes a distally-facing aperture 440 coupled to the internal chamber 436. The aperture 440 permits blood to enter the internal chamber 436, and the aperture 440 thereby permits the pressure sensor 438 to sense the pressure of the blood. The collar 434 further includes a transversely-facing aperture 441, and the distally-facing aperture 440 and the transversely-facing aperture 441 facilitate blood flow through the collar 434 and thereby reduce thrombi formation. In some embodiments, the collar 434 includes one or more additional apertures, such as transversely-facing apertures. Such apertures may originate from different angles on the collar 434 to facilitate blood flow. More specifically, such apertures may extend diagonally, or at an acute angle, relative to the longitudinal axis of the internal chamber 436. Such apertures can have various shapes, such as circular, cylindrical, or the apertures may be elongated slots.

The collar 434 extends at least partially around the catheter 426. The collar 434 may be coupled to the catheter 426 via an outer jacket (not shown) at least partially surrounding the collar 434 and the catheter 426, crimping, one or more adhesives, and/or one or more weldments (not shown).

Figure 9:
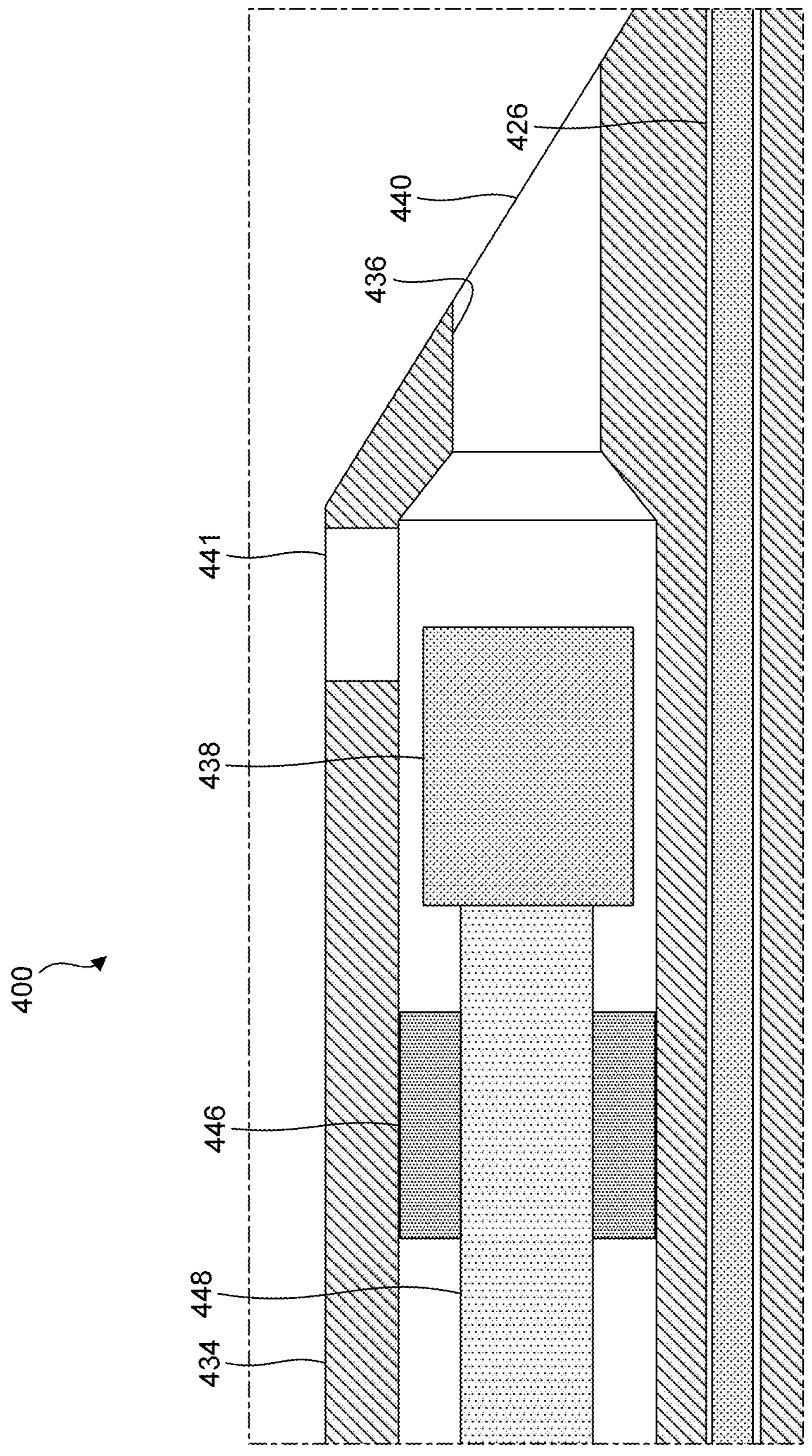
FIG. 9 is a detail view of the illustrative percutaneous circulatory support device within line 9-9 of FIG. 8.

With continued reference to FIG. 8 and additional reference to FIG. 9, the collar 434 may also carry a sensor mount 446 within the internal chamber 436. The sensor mount 446 facilitates supporting the pressure sensor 438 apart from the walls of the collar 434 (that is, the sensor mount 446 centers the pressure sensor 438 within the internal chamber 436), which in turn facilitates high-accuracy pressure sensing. The pressure sensor 438 may be adhered to the sensor mount 446.

With continued reference to FIGS. 8 and 9, the sensor assembly 432 further includes a sensor cable 448 coupled to the pressure sensor 438. The sensor cable 448 may operably couple the pressure sensor to the controller (not shown). As illustrated, the sensor cable 448 may extend through the sensor mount 446 and a proximally-facing aperture 449 (FIG. 8) of the collar 434.

Referring again to FIG. 8, the collar 434 supports the pressure sensor 438 relatively far from an outer surface 451 of the catheter 426, where blood flow is relatively slow. As a result, the collar 434 facilitates blood flow therethrough and thereby reduces thrombi formation. In some embodiments, the pressure sensor 438 is disposed apart from the outer surface 451 of the catheter 426 by at least 0.003 inches, and more specifically by at least 0.001 inches.

With continued reference to FIG. 8, an outer surface 452 of the collar 434 may be shaped to inhibit eddy formation in blood flow near the collar 434. More specifically, the outer surface 452 of the collar 434 may include a tapering distal portion 454 and tapering proximal portion 456. The tapering distal portion 454 and tapering proximal portion 456 may be separated by a non-tapering, or cylindrical, portion 458. As illustrated, the tapering distal portion 454 may form the distally-facing aperture 440 and the tapering proximal portion 456 may form the proximally-facing aperture 449. The tapering distal portion 454 may have a greater slope than the tapering proximal portion 456. Stated another way, the tapering distal portion 454 has a first slope, the tapering proximal portion 456 has a second slope, and the first slope may be greater than the second slope. In other embodiments, the outer surface 452 of the collar 434 may have different shapes. For example, the tapering distal portion 454 and the tapering proximal portion 456 may have equal slopes.

A method of manufacturing the percutaneous circulatory support device 400 may be as follows. The impeller 412 is positioned within the impeller housing 402 such that the impeller 412 is rotatable relative to the impeller housing 402. The impeller 412 is operably coupled to the motor 405, and the catheter 426 is positioned adjacent to the motor housing 404. The pressure sensor 438 and the sensor cable 448 are then coupled to the collar 434 such that the sensor 438 is positioned within the internal chamber 436 of the collar 434 and the sensor cable 448 extends from the proximally-facing aperture 449. The collar 434 and the pressure sensor 438 within the collar 434 are then advanced distally along the catheter 426. Next, the collar 434 is coupled to the catheter 426 by forming an outer jacket (not shown) at least partially surrounding the collar 434 and the catheter 426, crimping the collar 434, applying one or more adhesives, and/or forming one or more weldments (not shown).

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A percutaneous circulatory support device, comprising:

a housing comprising an inlet and an outlet;

an impeller disposed within the housing, the impeller configured to rotate relative to the housing to cause blood to flow into the inlet, through the housing, and out of the outlet;

a motor operably coupled to the impeller, the motor configured to rotate the impeller relative to the housing;

a catheter coupled to the motor;

a collar coupled to the catheter and disposed proximally relative to the housing, the collar comprising an internal chamber with a distally-facing aperture and a transversely-facing aperture, wherein the distally-facing aperture opens into the internal chamber and the transversely-facing aperture opens into the internal chamber, wherein the distally-facing aperture is positioned distal of the transversely-facing aperture; and a pressure sensor disposed within the internal chamber of the collar.

2. The percutaneous circulatory support device of claim 1, wherein the collar further comprises an outer surface, the outer surface comprising a tapering distal portion forming the distally-facing aperture.

3. The percutaneous circulatory support device of claim 1, wherein the transversely-facing aperture is a first transversely-facing aperture, and the collar further comprises one or more additional transversely-facing aperture coupled to the internal chamber.

4. The percutaneous circulatory support device of claim 1, further comprising a sensor mount disposed within the internal chamber of the collar and coupled to the pressure sensor.

5. The percutaneous circulatory support device of claim 4, wherein the pressure sensor is adhered to the sensor mount.

6. The percutaneous circulatory support device of claim 1, further comprising a sensor cable coupled to the pressure sensor.

7. The percutaneous circulatory support device of claim 6, wherein the collar further comprises a proximally-facing aperture coupled to the internal chamber, the sensor cable extending through the proximally-facing aperture.

8. The percutaneous circulatory support device of claim 7, wherein the collar further comprises an outer surface, the outer surface comprising a tapering proximal portion forming the proximally-facing aperture.

9. The percutaneous circulatory support device of claim 1, wherein the collar further comprises an outer surface, the outer surface comprising a tapering distal portion and a tapering proximal portion.

10. The percutaneous circulatory support device of claim 9, wherein the tapering distal portion has a first slope, the tapering proximal portion has a second slope, and the first slope is greater than the second slope.

11. The percutaneous circulatory support device of claim 1, wherein the pressure sensor comprises one of an optical pressure sensor and an electrical pressure sensor.

12. The percutaneous circulatory support device of claim 1, wherein a central longitudinal axis extending through the internal chamber also extends through the distally-facing aperture.

13. The percutaneous circulatory support device of claim 1, wherein at least a portion of the transversely-facing aperture is radially over a portion of the pressure sensor.

14. The percutaneous circulatory support device of claim 1, wherein the collar defines an outer surface parallel to a longitudinal axis of the catheter, wherein an entirety of the transversely-facing aperture extends through the outer surface of the collar.

15. The percutaneous circulatory support device of claim 1, wherein the collar circumferentially surrounds the catheter such that the catheter extends distal of the collar and the catheter extends proximal of the collar.

16. A percutaneous circulatory support device, comprising:
- a housing comprising an inlet and an outlet;
- an impeller disposed within the housing, the impeller configured to rotate relative to the housing to cause blood to flow into the inlet, through the housing, and out of the outlet;
- a motor operably coupled to the impeller, the motor configured to rotate the impeller relative to the housing;
- a catheter coupled to the motor;
- a collar circumferentially surrounding the catheter and coupled to the catheter proximally relative to the housing, the collar comprising:
  - an internal chamber;
  - a distally-facing aperture opening into the internal chamber;
  - a proximally-facing aperture opening into the internal chamber;
  - a transversely-facing aperture opening into the internal chamber and disposed proximal of the distally-facing aperture;
- a pressure sensor disposed within the internal chamber of the collar; and
- a sensor cable coupled to the pressure sensor, the sensor cable extending through the proximally-facing aperture.

17. The percutaneous circulatory support device of claim 16, wherein the pressure sensor is disposed apart from an outer surface of the catheter by at least 0.001 inches.

18. The percutaneous circulatory support device of claim 16, wherein a central longitudinal axis extending through the internal chamber also extends through the distally-facing aperture.

19. A method of manufacturing a percutaneous circulatory support device, the method comprising:
- positioning an impeller within a housing such that the impeller is rotatable relative to the housing;
- operably coupling a motor to the impeller;
- coupling a catheter to the motor;
- coupling a pressure sensor to a collar; and thereafter
- coupling the collar and the pressure sensor to the catheter proximally of the motor, wherein the collar includes an internal chamber with the pressure sensor disposed within the internal chamber, the collar further including a distally-facing aperture and a transversely-facing aperture, wherein the distally-facing aperture opens into the internal chamber and the transversely-facing aperture opens into the internal chamber, wherein the distally-facing aperture is positioned distal of the transversely-facing aperture.

20. The method of claim 19, wherein coupling the collar and the pressure sensor to the catheter comprises distally advancing the collar and the pressure sensor along the catheter with the collar circumferentially surrounding the catheter.

* * * * *